United States Patent [19]

Beach et al.

[11] 4,272,407

[45] Jun. 9, 1981

[54] METAL MODIFIED REFRACTORY METAL OXIDE/SILICA SUPPORTED NICKEL CLUSTER CATALYST

[75] Inventors: David L. Beach; Thaddeus P. Kobylinski, both of Gibsonia, Pa.

[73] Assignee: Gulf Research & Development Company, Pittsburgh, Pa.

[21] Appl. No.: 151,951

[22] Filed: May 21, 1980

[51] Int. Cl.³ .............................................. B01J 31/12
[52] U.S. Cl. ............................ 252/430; 252/429 R; 252/431 R; 252/431 C; 585/511; 585/521
[58] Field of Search ............... 252/429 R, 430, 431 R, 252/431 C

[56] References Cited

U.S. PATENT DOCUMENTS

| | | | |
|---|---|---|---|
| 3,134,824 | 5/1964 | Walker et al. | 252/430 X |
| 3,424,816 | 1/1969 | McClure et al. | 585/511 |
| 3,459,826 | 8/1969 | Barnett et al. | 252/430 X |
| 3,527,838 | 9/1970 | Barnett et al. | 252/430 X |
| 3,530,197 | 9/1970 | McClure | 252/431 R X |
| 3,532,765 | 10/1970 | Barnett et al. | 252/430 X |
| 3,686,159 | 8/1972 | Bauer et al. | 252/431 P X |
| 3,736,264 | 5/1973 | Chauvin | 252/429 R |
| 4,024,202 | 5/1977 | Burnham | 260/439 R X |

FOREIGN PATENT DOCUMENTS

1060399  7/1959  Fed. Rep. of Germany.
1033161  6/1966  United Kingdom.

OTHER PUBLICATIONS

Bamford, J. Polym. Sci., Part C, No. 4, pp. 1571–1587.
Ichikawa, J. Chem. Soc., Chem. Comm., 1976, pp. 26–27.
Bamford et al., Chem. Ab., vol. 57, col. 13961 (1962).
Ichikawa, J. Chem. Soc., Chem. Comm., 1978, pp. 566–567.
Lapidus et al., Chem. Ab., vol. 82, p. 239, paragraph 7897z (1975).
Lapidus et al., Chem. Ab., vol. 85, p. 583, paragraph 93717g (1976).
Smith et al., J. Molecular Catalysis, 2, 1977, pp. 229–241.

*Primary Examiner*—Patrick Garvin
*Attorney, Agent, or Firm*—Deane E. Keith; Forrest D. Stine; Joseph J. Carducci

[57] ABSTRACT

A catalyst that is highly active in the oligomerization of lower olefins such as ethylene is produced by contacting (a) a refractory metal oxide/silica support, such as alumina/silica wherein the silica content of the support is from about 2 to about 95 weight percent and the metal oxide content of the support is from about 5 to about 98 percent with (b) a solution of a basic metal and then (c) contacting the resulting metal modified support with a tris(cyclopentadienyl)trinickel dicarbonyl.

58 Claims, No Drawings

METAL MODIFIED REFRACTORY METAL OXIDE/SILICA SUPPORTED NICKEL CLUSTER CATALYST

CROSS-REFERENCES TO RELATED APPLICATIONS

Reference is made to applicants' following U.S. applications:

U.S. patent application Ser. No. 151,948, filed May 21, 1980, entitled "Refractory Metal Oxide/Silica Supported Nickel Cluster Catalyst."

U.S. patent application Ser. No. 151,961, filed May 21, 1980, entitled "Process for the Oligomerization of Ethylene."

U.S. patent application Ser. No. 151,950, filed May 21, 1980, entitled "Process for the Oligomerization of Propylene and Higher Olefins."

U.S. patent application Ser. No. 151,953, filed May 21, 1980, entitled "Alkylation of Aromatics with Propylene and Higher Olefins."

U.S. patent application Ser. No. 151,952, filed May 21, 1980, entitled "Use of Metal Modified Refractory Metal Oxide/Silica Supported Nickel Cluster Catalyst to Oligomerize Ethylene."

The disclosures of the foregoing applications are hereby incorporated by reference.

FIELD OF THE INVENTION

The present invention relates to a metal modified refractory metal oxide/silica supported nickel cluster catalyst. More particularly, this invention relates to a catalyst obtained by contacting a refractory metal oxide/silica support with a solution of a basic metal and then with a nickel cluster which catalyst is characterized by a high activity for the oligomerization of ethylene.

DESCRIPTION OF THE PRIOR ART

It is well known in the art to use a variety of catalysts to oligomerize ethylene to higher molecular weight olefins. The term "oligomerize" has been employed, and is employed herein to describe the conversion of lower olefins such as ethylene to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls and the "Ziegler-Natta" types consisting of aluminum alkyl halides and titanium halides. Major disadvantages of aluminum alkyl catalysts are their highly reactive and pyrophoric nature and the fact that they must be used at relatively high temperatures, e.g., 200°–275° C. and pressures, e.g., 2000–4000 psig (13,790 to 27,580 kPa). Although much milder reaction conditions are used when the aluminum alkyls are used in conjunction with titanium halides, the reaction rates of both of these prior art types of catalysts are not as high as desired.

Several heterogeneous supported cyclopentadienyl nickel catalysts have been employed to oligomerize ethylene to higher molecular weight olefins. One such process described in U.S. Pat. No. 3,459,826 to Barnett et al employs nickelocene, i.e., bis(cyclopentadienyl)-nickel, and an inorganic oxide catalyst support. This process, however, requires pretreatment with elemental hydrogen and yields 84% dimer and trimer. Related processes using ($\pi$-cyclopentenyl)cyclopentadienyl-nickel are described in U.S. Pat. No. 3,527,838 and U.S. Pat. No. 3,532,765, both to Barnett et al.

A non-pyrophoric nickel-supported catalyst is described by Masaru Ichikawa in an article entitled "Preparation and Catalytic Activities of Supported Nickel Clusters on a Silica Surface," J. Chem. Soc., Chem. Comm. (1976), pages 26 and 27. This article discloses tris(cyclopentadienyl)trinickel dicarbonyl and other nickel cluster compounds deposited on silica gel or Vycor glass No. 7930 followed by heating at 120° C. as catalysts for olefin hydrogenation and for the "oxo" reaction. Vycor glass No. 7930 is understood to be 95.6 weight percent silica, 1.0 weight percent alumina, 2.25 weight percent boric acid, the remaining 0.25 weight percent being unidentified contaminants.

SUMMARY OF THE INVENTION

A non-pyrophoric, nickel supported catalyst has now been found that is highly active at relatively low operating temperatures and pressures in the oligomerization of ethylene. This catalyst can be produced by contacting (a) a refractory metal oxide/silica oxide support such as alumina/silica wherein the silica content of the support is from about 2 to about 95 weight percent and the metal oxide content of the support is from about 5 to about 98 percent with (b) an aqueous or alcoholic solution of a soluble salt of a basic metal, e.g., an alkali metal, an alkaline earth metal or a lanthanide metal to form a metal modified support. The resulting metal modified support is contacted with a tris(cyclopentadienyl)-trinickel dicarbonyl.

The metal oxide associated with the silica in the support may be defined by the formula $M_xO_y$ wherein M is aluminum, magnesium, zirconium or thorium, x is an integer of from 1 to 2 and y is an integer of from 1 to 3. Specific examples of such compounds include $Al_2O_3$, $MgO$, $ZrO_2$, $ThO_2$, etc.

The tris(cyclopentadienyl)trinickel dicarbonyl used herein has the structure:

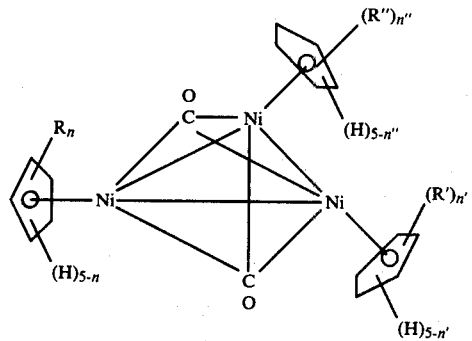

wherein R, R' and R" can be the same or different $C_1$ to $C_{20}$ inclusive, hydrocarbon radicals, and n, n' and n" can be the same or different integers of 0 to 5, inclusive. The R, R' and R" hydrocarbon radicals can be saturated or unsaturated, they can include aliphatic, alicyclic and aromatic radicals such as methyl, ethyl, propyl, butyl, pentyl, cyclopentyl, cyclohexyl, allyl, phenyl and naphthyl radicals. One or more of the cyclopentadienyl moieties in the foregoing tris(cyclopentadienyl)trinickel dicarbonyl can be substituted so as to form an indenyl moiety or a fluorenyl moiety.

Specific examples of nickel clusters which can be used include:

tris(cyclopentadienyl)trinickel dicarbonyl,
tris(methylcyclopentadienyl)trinickel dicarbonyl,
(methylcyclopentadienyl)bis(cyclopentadienyl)trinickel dicarbonyl,
bis(methylcyclopentadienyl)(cyclopentadienyl)trinickel dicarbonyl,
tris(pentamethylcyclopentadienyl)trinickel dicarbonyl,
(pentamethylcyclopentadienyl)bis(cyclopentadienyl)trinickel dicarbonyl,
bis(pentamethylcyclopentadienyl)(cyclopentadienyl)trinickel dicarbonyl,
(methylcyclopentadienyl)bis(pentamethylcyclopentadienyl)trinickel dicarbonyl,
bis(methylcyclopentadienyl)(pentamethylcyclopentadienyl)trinickel dicarbonyl,
tris(ethylcyclopentadienyl)trinickel dicarbonyl,
(ethylcyclopentadienyl)bis(cyclopentadienyl)trinickel dicarbonyl,
bis(ethylcyclopentadienyl)(cyclopentadienyl)trinickel dicarbonyl,
tris(n-propylcyclopentadienyl)trinickel dicarbonyl,
tris(iso-propylcyclopentadienyl)trinickel dicarbonyl,
tris(butylcyclopentadienyl)trinickel dicarbonyl,
tris(pentylcyclopentadienyl)trinickel dicarbonyl,
tris(indenyl)trinickel dicarbonyl,
(indenyl)bis(cyclopentadienyl)trinickel dicarbonyl,
bis(indenyl)(cyclopentadienyl)trinickel dicarbonyl,
(indenyl)bis(methylcyclopentadienyl)trinickel dicarbonyl,
bis(indenyl)(methylcyclopentadienyl)trinickel dicarbonyl,
(indenyl)bis(pentamethylcyclopentadienyl)trinickel dicarbonyl,
bis(indenyl)(pentamethylcyclopentadienyl)trinickel dicarbonyl, wherein the indenyl moiety has the structure:

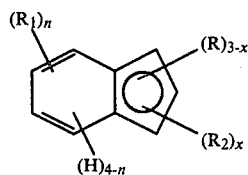

wherein ($R_1$) and ($R_2$) are the same or different $C_1$ to to $C_{10}$ hydrocarbon radicals, n is an integer of 0 to 4, and x is an integer of 0 to 3, tris(fluorenyl)trinickel dicarbonyl,
(fluorenyl)bis(cyclopentadienyl)trinickel dicarbonyl,
bis(fluorenyl)(cyclopentadienyl)trinickel dicarbonyl,
(fluorenyl)bis(methylcyclopentadienyl)trinickel dicarbonyl,
bis(fluorenyl)methylcyclopentadienyl)trinickel dicarbonyl,
(fluorenyl)bis(pentamethylcyclopentadienyl)trinickel dicarbonyl,
bis(fluorenyl)(pentamethylcyclopentadienyl)trinickel dicarbonyl, wherein the fluorenyl moiety has the structure:

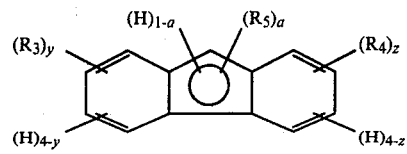

wherein ($R_3$), ($R_4$) and ($R_5$) can be the same or different $C_1$ to $C_{10}$ hydrocarbon radicals; y and z can be the same or different integers of 0 to 4; and a is 0 or 1. The ($R_1$), ($R_2$), ($R_3$), ($R_4$) and ($R_5$) hydrocarbon radicals can be the same or different, saturated or unsaturated and include the hydrocarbon radicals as described for R, R' and R''.

When used to oligomerize ethylene the catalysts of the present invention are characterized by a relatively high reaction rate at moderate temperatures and pressures. Their use results in the production of relatively high proportions of desirable trimer, tetramer, pentamer, and higher olefinic products. Additionally, the present catalysts do not exhibit pyrophoric behavior and can be used at lower temperatures and pressures than conventional aluminum alkyl catalysts.

DESCRIPTION OF THE PREFERRED EMBODIMENTS

A suitable support for use in the preparation of a catalyst composition of this invention is a metal oxide/silica support wherein the silica content is from about 2 to about 95 weight percent and the metal oxide content is from about 5 to about 98 weight percent. Preferably, the support comprises from about 15 to about 92 weight percent silica and about 10 to about 85 weight percent metal oxide; and most preferably from about 80 to about 92 weight percent silica and from about 10 to about 20 weight percent metal oxide. The metal oxide/silica supports include synthetic materials as well as acid-treated clays or even the crystalline alumina silicates known as molecular sieves, so long as the silica and alumina contents are within the ranges specified. Thus, any of the commercially available metal oxide/silicas having the proper silica to metal oxide ratios can suitably be used to prepare the compositions of this invention. The preferred alumina/silicas are coprecipitated from aqueous or alcoholic solutions of a silicate such as sodium silicate or silicic acid and an aluminum salt such as aluminum nitrate, aluminum sulfate or aluminum chloride. For example, an aqueous solution of silicic acid and aluminum nitrate produces a coprecipitate when treated with ammonium hydroxide at a controlled pH of about 8. Differing physical properties of the coprecipitates result by varying the pH during precipitation. The precipitates are an intimate comixture of silicon and aluminum oxides.

The support defined above is first contacted with an aqueous or alcoholic solution, preferably aqueous, of a soluble salt whose cationic portion can be (1) an alkali metal, (2) an alkaline earth metal or (3) a lanthanide, and whose anionic portion can be (1) a halide, (2) a nitrate, (3) an acetate or (4) an acetylacetonate. By "an alkali metal" we mean to include lithium, sodium and potassium; by "an alkaline earth metal" we mean to include beryllium, magnesium, calcium, strontium and barium; and by "a lanthanide" we mean to include lanthanum, cerium, europium and holmium. By "halide" we mean to include fluoride, chloride, bromide and iodide. Specific examples of such soluble salts that can be used herein include lithium fluoride, lithium chloride, lithium bromide, lithium iodide, lithium nitrate, lithium acetate, lithium acetylacetonate and the specific compounds mentioned above but wherein lithium is replaced with the remaining specific alkali metals, alkaline earth metals and lanthanide metals mentioned above. If an alcoholic solution is used the alcohol can be methanol, ethanol, n-propanol or isopropanol. The concentration of the above salt in the solution is not critical and can vary over a wide range. Thus, the concentration of the salt in the solution can range from about 0.01 to about 1.0 molar, preferably from about 0.05 to about 0.5. The volume of solution per weight of support is also not critical and can range from about one to about 50 milliliters of solution per gram of support, preferably from about 2.5 to about 25 milliliters of solution per gram of support. The support is stirred in the solution for about one to about 24 hours, or even longer, at a temperature of about 20° to about 100° C., preferably about 20° to about 50° C., sufficient to transfer the metal component of the salt from the solution onto the support. The solid metal modified refractory metal oxide/silica support is then recovered from the slurry by filtration, decantation, etc. and dried to remove residual water or alcohol. The amount of metal in the modified refractory metal oxide/silica support obtained at the end of this step will fall within the range of about 0.1 to about 5.0 weight percent, based on the final support, preferably about 0.5 to about 2.5 weight percent. The catalyst used herein, as modified, results in an unexpected increase in catalytic activity.

Preferably, the support is calcined prior to contact with the nickel cluster as by heating at a temperature of from about 200° C. to about 800° C. and, more preferably, from about 450° C. to about 650° C. for a period of from about one to about 24 hours, or even longer, but preferably about four to about 12 hours. The calcining operation can be conducted in air, but is preferably conducted in an inert atmosphere such as in a stream of argon or nitrogen. Following the calcining operation, the support is cooled slowly in an inert atmosphere and stored in the absence of air.

The calcined support is then contacted in the absence of air with the nickel cluster, that is, a tris(cyclopentadienyl)trinickel dicarbonyl. The nickel cluster defined by the chemical formula $(\eta^5\text{-}C_5H_5)_3Ni_3(CO)_2$, wherein $\eta$ is the Greek letter eta, used herein, can be prepared by the method of E. O. Fischer et al described in Chem. Ber., 91, 1725 (1958). This compound is a solid at room temperature and is not sensitive to air. The structure of the nickel cluster consists of a triangle of nickel atoms with a cyclopentadienyl ligand bonded to each nickel in a pentahapto fashion and two triply-bridging carbon monoxide ligands. This complex has the structure represented above when each of n, n' and n'' has a value of 0.

One method of contacting the support with the nickel cluster is to use a solution of the nickel cluster in a liquid hydrocarbon solvent which is non-reactive. Examples of such solvents include pentane, hexane, heptane, cyclopentane, cyclohexane, benzene, toluene, and xylene. The amount of nickel cluster used is not critical and can vary widely as long as the nickel content of the product obtained from the reaction of the nickel cluster with the support is within the range of about 0.001 to about five weight percent, preferably within the range of about 0.05 to about two weight percent.

The nickel cluster and the support are contacted at a temperature of from about 20° to about 200° C. for a period of about 10 minutes to about 12 hours and, more preferably, for about 15 minutes to about one hour at a temperature of from about 20° to about 100° C. The temperature and time can vary widely depending upon the solubility-temperature profile of the solvent and nickel cluster. They can be contacted in any suitable reaction vessel such as an autoclave.

The nickel cluster has a low solubility in certain aliphatic and alicyclic solvents such as heptane and cyclohexane. This may result in a very slow transfer and/or an incomplete transfer of the nickel cluster from solution to the support. Thus, when using such solvents, a different method of contacting the nickel cluster and the support is preferably used. According to this method, instead of adding the nickel cluster as a solution to the reaction chamber, it is charged as a solid with the support. After purging the reaction chamber with an inert gas such as argon or nitrogen, the solvent is then added to the reaction chamber.

Following the necessary contact time to effect deposition of the nickel cluster onto the support, the resultant catalyst composition can be separated from the solvent diluent and stored, preferably in an inert atmosphere, until ready for use. Separation can be accomplished by conventional techniques such as filtration, centrifugation, and decantation. The catalyst composition can be dried in an inert atmosphere. Alternatively, the catalyst composition can be used to oligomerize an olefin such as ethylene in the solvent diluent in which it was prepared.

If the catalyst is to be used in the oligomerization of an olefin, it is preferred to activate it or preactivate it prior to contact with the olefin, unless temperatures exceeding 100° C. were used in the reaction of the nickel cluster with the support in which case the activation or preactivation is unnecessary. Activation and preactivation of the catalyst can be accomplished by heating it in an inert atmosphere at a temperature between about 70° and about 200° C., preferably between about 100° to about 170° C., for from about five minutes to about 4 hours, or longer, but preferably about 20 minutes to about one hour. The term "activation" as used herein refers to an operation performed in situ in the oligomerization reactor prior to the addition of the olefin; and the term "preactivation" refers to an operation performed external to the oligomerization reactor.

The catalyst compositions of this invention possess several advantages over prior art oligomerization catalysts. Thus, their use in the oligomerization of ethylene avoids the use of the highly reactive, pyrophoric aluminum alkyls. Nickel oligomerization catalysts ordinarily do not result in the production of significant amounts of higher olefins than dimers. The novel catalyst herein, however, when used to oligomerize ethylene results in the production of significant amounts of oligomers higher than dimers, that is, oligomers having up to about 20 carbon atoms. Moreover, higher reaction rates are attained at lower temperatures and pressures than with prior art catalysts.

The compositions of this invention are also useful as alkylation catalysts as shown in our U.S. patent application Ser. No. 151,953, entitled "Alkylation of Aromatics with Propylene and Higher Olefins," filed concurrently herewith, and for the isomerization of alpha-olefins to internal olefins. When used to isomerize alpha-olefins, it is not necessary to activate or preactivate the catalyst.

The following examples illustrate the best mode contemplated for carrying out this invention. In the examples, the amount of nickel in the catalyst is reported as weight percent elemental nickel based upon the total catalyst weight. The activities reported were calculated based upon the weight of elemental nickel supplied by the nickel complex. All percentages are by weight unless otherwise indicated.

EXAMPLE 1

A support was prepared by isolating a 4.0 gram sample of an alumina/silica mixture comprising 87 weight percent silica and 12 weight percent alumina through 100 mesh. The support, having a surface area of 425–450 m$^2$/g., was stirred for about 18 hours at 22° C. in a glass bottle with 50 ml. of 0.1 M aqueous potassium acetate. The suspension was filtered through a fritted glass funnel and the solid washed twice with 25 ml. portions of distilled water. The resulting potassium-modified alumina/silica support was dried overnight in vacuuo, then calcined at 550° C. for 20 hours fluidized in an argon stream. The support was found to contain 1.28 weight percent potassium. Subsequently, 2.05 grams of the calcined support were transferred under argon to a 300 cc. Magnedrive autoclave which had been previously purged with argon. The autoclave was sealed and again purged with argon by three successive argon pressuring-venting cycles. Into a separate clean, dry bottle was accurately weighed 0.0188 gram of tris(cyclopentadienyl)trinickel dicarbonyl. The bottle was fitted with a rubber septum and purged with argon for greater than 0.5 hour. Dry, oxygen-free benzene (50 ml.) which had been purified by distillation under argon from sodium benzophenone ketyl was syringed into the bottle and the resulting solution was syringed under argon into the autoclave containing the support. The contents of the autoclave were stirred at 500 r.p.m. at 22° C. for 0.5 hour to allow adsorption of the tris(cyclopentadienyl)trinickel dicarbonyl onto the support. Heating was commenced and the contents of the autoclave maintained at 150° C. for 30 minutes. The weight percent of nickel on the support was 0.38. In order to demonstrate the effectiveness of this catalyst in the oligomerization of ethylene, ethylene was added to the autoclave to a total pressure of 500 psig (3448 kPa), as needed, to always maintain a pressure of 450–500 psig (3103–3448 kPa). The temperature was maintained at 150°±2° C. After 1.0 hour the autoclave was rapidly cooled to 20° C. and the product mixture removed and analyzed by gas chromatographic techniques. The results are reported in Table I. An activity of 4643 grams of oligomer per gram of nickel per hour was found.

TABLE I

| Olefin | Selectivity (Percent) |
|---|---|
| C-4 | 49 |
| C-6 | 33 |
| C-8 | 12 |
| C-10 | 5 |
| C-12 | 0.5 |
| ≧C-14 | 0.5 |

| | C-4 Composition (Percent) |
|---|---|
| 1-butene | 21 |
| trans-2-butene | 46 |
| cis-2-butene | 33 |

EXAMPLE 2

A support was prepared by isolating a 5.0 gram sample of an alumina/silica mixture comprising 87 weight percent silica and 12 weight percent alumina through 100 mesh. The support, having a surface area of 425–450 m$^2$/g., was stirred for about 23 hours at 22° C. with 50 ml. of 0.1 M aqueous Mg(NO$_3$)$_2$ which had been prepared by dissolving 2.56 grams of Mg(NO$_3$)$_2$ 6H$_2$O in 100 ml. of distilled water. The suspension was filtered through a fritted glass funnel and the solid washed three times with 25 ml. portions of distilled water. The resulting magnesium-modified alumina/silica was dried overnight in vacuuo, placed in a vertically mounted quartz tube, fluidized with a stream of argon and calcined at 550° C. for about 20 hours. The support was found to contain 1.08 weight percent magnesium. Subsequently, 2.08 grams of the calcined support were transferred under argon to a 300 cc. Magnedrive autoclave which had been previously purged with argon. The autoclave was sealed and again purged with argon by three successive argon pressuring-venting cycles. Into a separate clean, dry bottle was accurately weighed 0.0100 gram of tris(cyclopentadienyl)trinickel dicarbonyl. The bottle was fitted with a rubber septum and purged with argon for greater than 0.5 hour. Dry, oxygen-free benzene (50 ml.) which had been purified by distillation under argon from sodium benzophenone ketyl was syringed into the bottle and the resulting solution was syringed under argon into the autoclave containing the support. The contents of the autoclave were stirred at 500 r.p.m. at 22° C. for 0.5 hour to allow adsorption of the tris(cyclopentadienyl)trinickel dicarbonyl onto the support. Heating was commenced and the contents of the autoclave maintained at 150° C. for 30 minutes. The weight percent of nickel on the support was 0.20. In order to demonstrate the effectiveness of this catalyst in the oligomerization of ethylene, the reactor contents were cooled to 70° C. and ethylene was added to the autoclave to a total pressure of 500 psig (3448 kPa), as needed, to always maintain a pressure of 450–500 psig (3103–3448 kPa). The temperature was maintained at 70° C. After 1.0 hour the autoclave was rapidly cooled to 20° C. and the product mixture removed and analyzed by gas chromatographic techniques. The results are reported in Table II. An activity of 14,083 grams of oligomer per gram of nickel per hour was found.

TABLE II

| Olefin | Selectivity (Percent) |
|---|---|
| C-4 | 60 |
| C-6 | 26 |
| C-8 | 8 |
| C-10 | 5 |
| C-12 | 2 |
| ≧C-14 | >1 |

| | C-4 Composition (Percent) |
|---|---|
| 1-butene | 44 |
| trans-2-butene | 32 |
| cis-2-butene | 24 |

EXAMPLE 3

A support was prepared by isolating a 5.0 gram sample of an alumina/silica mixture comprising 87 weight percent silica and 12 weight percent alumina through 100 mesh. The support, having a surface area of 425–450 m$^2$/g., was stirred for 23 hours at 22° C. with 50 ml. of 0.1 M aqueous LaCl$_3$ which had been prepared by dissolving 3.53 grams of LaCl$_3$ 6H$_2$O in 100 ml. of distilled water. The La-modified alumina/silica was washed, dried and calcined as described in Example 2 for the Mg-modified alumina/silica. The support was found to contain 0.8 weight percent lanthanum. Subsequently, 2.08 grams of the calcined support were transferred under argon to a 300 cc. Magnedrive autoclave which had been previously purged with argon. The autoclave was sealed and again purged with argon by three successive argon pressuring-venting cycles. Into a separate clean, dry bottle was accurately weighed 0.0093 gram of tris(cyclopentadienyl)trinickel dicarbonyl. The bottle was fitted with a rubber septum and purged with argon for greater than 0.5 hour. Dry, oxygen-free benzene (47 ml.) which had been purified by distillation under argon from sodium benzophenone ketyl was syringed into the bottle and the resulting solution was syringed under argon into the autoclave containing the support. The contents of the autoclave were stirred at 500 r.p.m. at 22° C. for 0.5 hour to allow adsorption of the tris(cyclopentadienyl)trinickel dicarbonyl onto the support. Heating was commenced and the contents of the autoclave maintained at 150° C. for 30 minutes. The weight percent of nickel on the support was 0.18. In order to demonstrate the effectiveness of this catalyst in the oligomerization of ethylene, the reactor contents were cooled to 70° C. and ethylene was added to the autoclave to a total pressure of 500 psig (3448 kPa), as needed, to always maintain a pressure of 450-500 psig (3103-3448 kPa). The temperature was maintained at 70° C. After 1.0 hour the autoclave was rapidly cooled to 20° C. and the product mixture removed and analyzed by gas chromatographic techniques. The results are reported in Table III. An activity of 18,353 grams of oligomer per gram of nickel per hour was found.

TABLE III

| Olefin | Selectivity (Percent) |
|---|---|
| C-4 | 57 |
| C-6 | 28 |
| C-8 | 9 |
| C-10 | 5 |
| C-12 | 0.5 |
| ≧C-14 | >1 |

| | C-4 Composition (Percent) |
|---|---|
| 1-butene | 43 |
| trans-2-butene | 33 |
| cis-2-butene | 24 |

EXAMPLE 4

In order to demonstrate the improved effectiveness of the metal modified alumina/silica supported nickel cluster catalysts of this invention, an alumina/silica supported catalyst was prepared which was not metal modified. Thus, an alumina/silica support was prepared by calcining an alumina/silica mixture comprising 87 weight percent silica and 12 weight percent alumina under argon at 550° C. for 24 hours. Subsequently, 1.50 grams of the calcined support were transferred under argon to a 300 cc. Magnedrive autoclave which had been previously purged with argon. The autoclave was sealed and again purged with argon by three successive argon pressuring-venting cycles. Into a separate clean, dry bottle was accurately weighed 0.0560 gram of tris(cyclopentadienyl)trinickel dicarbonyl. The bottle was fitted with a rubber septum and purged with argon for greater than 0.5 hour. Dry, oxygen-free benzene which had been purified by distillation under argon from sodium benzophenone ketyl was syringed into the bottle and the resulting solution comprising a total volume of about 98 ml. was syringed under argon into the autoclave containing the support. The contents of the autoclave were stirred at 500 r.p.m. at 22° C. for 0.5 hour to allow adsorption of the tris(cyclopentadienyl)trinickel dicarbonyl onto the support. Heating was commenced and the contents of the autoclave maintained at 150° C. for 30 minutes. The weight percent of nickel on the support was 1.48. Ethylene was added to the autoclave to a total pressure of 500 psig (3448 kPa), as needed, to always maintain a pressure of 450-500 psig (3103-3448 kPa). The temperature was maintained at 150°±2° C. After 1.0 hour the autoclave was rapidly cooled to 20° C. and the product mixture removed and analyzed by gas chromatographic techniques. The results are reported in Table IV. An activity of 1576 grams of oligomer per gram of nickel per hour was found.

TABLE IV

| Olefin | Selectivity (Percent) |
|---|---|
| C-4 | 53 |
| C-6 | 24 |
| C-8 | 13 |
| C-10 | 7 |
| C-12 | 2 |
| C-14 | 1 |
| C-16 –C-20 | trace |

| | C-4 Composition (Percent) |
|---|---|
| 1-butene | 11.0 |
| trans-2-butene | 53.4 |
| cis-2-butene | 35.6 |

It will be seen from the above that when a catalyst obtained by contacting a refractory metal oxide/silica support with a solution of a basic metal and then with a nickel cluster is used to oligomerize ethylene, rather than a similar catalyst which has not been contacted with a solution of a basic metal, the catalyst possesses a much higher activity. Thus, when the catalyst obtained by contacting a refractory metal oxide/silica support with a nickel cluster was initially contacted with a solution of a potassium salt in Example 1, a magnesium salt in Example 2 and a lanthanum salt in Example 3, a much greater increase in activity was obtained than in Example 4 wherein the catalyst was not treated initially with a solution of a basic metal salt.

Although the invention has been described in considerable detail with particular reference to certain preferred embodiments thereof, variations and modifications can be effected within the spirit and scope of the invention as described hereinbefore, and as defined in the appended claims.

We claim:

1. A catalyst composition obtained by contacting (1) a refractory metal oxide/silica support wherein the silica content of said support is from about 2 to about 95 weight percent and the metal oxide content of said support is from about 5 to about 98 weight percent with (2) a solution of a soluble salt whose cationic portion is selected from the group consisting of an alkali metal, an alkaline earth metal and a lanthanide and whose anionic portion is selected from the group consisting of a halide, a nitrate, an acetate and an acetylacetonate and (3) then contacting the metal modified support with a tris(cyclopentadienyl)trinickel dicarbonyl.

2. A catalyst composition as defined in claim 1 wherein said tris(cyclopentadienyl)trinickel dicarbonyl has the structure:

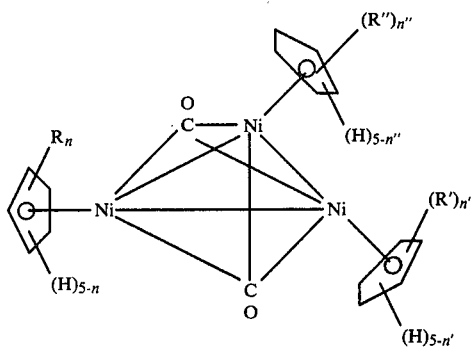

wherein R, R' and R" are the same or different $C_1$ to $C_{20}$ hydrocarbon radicals and n, n' and n" can be the same or different integers of 0 to 5, inclusive.

3. A catalyst composition as defined in claim 2 wherein the metal oxide component of said support has the formula $M_xO_y$, wherein M is aluminum, magnesium, zirconium or thorium, x is an integer of from 1 to 2 and y is an integer of from 1 to 3.

4. A catalyst composition as defined in claim 3 wherein the metal oxide is alumina.

5. A catalyst composition as defined in claim 1 wherein the silica content is from about 15 to about 92 weight percent and the metal oxide content is from about 10 to about 85 weight percent.

6. A catalyst composition as defined in claim 1 wherein the silica content is from about 80 to about 92 weight percent and the metal oxide content is from about 10 to about 20 weight percent.

7. A catalyst composition as defined in claim 4 wherein the silica content is from about 15 to about 92 weight percent and the alumina content is from about 10 to about 85 weight percent.

8. A catalyst composition as defined in claim 4 wherein the silica content is from about 80 to about 92 weight percent and the alumina content is from about 10 to about 20 weight percent.

9. A catalyst composition as defined in claim 4 wherein the silica content is about 87 weight percent and the alumina content is about 12 weight percent.

10. A catalyst composition as defined in claim 4 wherein the silica content is about 75 weight percent and the alumina content is about 25 weight percent.

11. A catalyst composition as defined in claim 1 wherein said tris(cyclopentadienyl)trinickel dicarbonyl is defined by the chemical formula $(\eta^5\text{—}C_5H_5)_3Ni_3(CO)_2$.

12. A catalyst composition as defined in claim 2 wherein said tris(cyclopentadienyl)trinickel dicarbonyl is defined by the chemical formula $(\eta^5\text{—}C_5H_5)_3Ni_3(CO)_2$.

13. A catalyst composition as defined in claim 3 wherein said tris(cyclopentadienyl)trinickel dicarbonyl is defined by the chemical formula $(\eta^5\text{—}C_5H_5)_3Ni_3(CO)_2$.

14. A catalyst composition as defined in claim 4 wherein said tris(cyclopentadienyl)trinickel dicarbonyl is defined by the chemical formula $(\eta^5\text{—}C_5H_5)_3Ni_3(CO)_2$.

15. A catalyst composition as defined in claim 5 wherein said tris(cyclopentadienyl)trinickel dicarbonyl is defined by the chemical formula $(\eta^5\text{—}C_5H_5)_3Ni_3(CO)_2$.

16. A catalyst composition as defined in claim 6 wherein said tris(cyclopentadienyl)trinickel dicarbonyl is defined by the chemical formula $(\eta^5\text{—}C_5H_5)_3Ni_3(CO)_2$.

17. A catalyst composition as defined in claim 7 wherein said tris(cyclopentadienyl)trinickel dicarbonyl is defined by the chemical formula $(\eta^5\text{—}C_5H_5)_3Ni_3(CO)_2$.

18. A catalyst composition as defined in claim 8 wherein said tris(cyclopentadienyl)trinickel dicarbonyl is defined by the chemical formula $(\eta^5\text{—}C_5H_5)_3Ni_3(CO)_2$.

19. A catalyst composition as defined in claim 9 wherein said tris(cyclopentadienyl)trinickel dicarbonyl is defined by the chemical formula $(\eta^5\text{—}C_5H_5)_3Ni_3(CO)_2$.

20. A catalyst composition as defined in claim 10 wherein said tris(cyclopentadienyl)trinickel dicarbonyl is defined by the chemical formula $(\eta^5\text{—}C_5H_5)_3Ni_3(CO)_2$.

21. A catalyst composition as defined in claim 1 wherein said support is calcined, prior to said contact with said tris(cyclopentadienyl)trinickel dicarbonyl at a temperature from about 200° to about 800° C. for about one to about 24 hours.

22. A catalyst composition as defined in claim 1 wherein said contact of said support with said tris(cyclopentadienyl)trinickel dicarbonyl is conducted in the absence of air at a temperature of about 20° to about 200° C.

23. A catalyst composition as defined in claim 1 wherein a solution of said tris(cyclopentadienyl)trinickel dicarbonyl is contacted with said support.

24. A catalyst composition as defined in claim 23 wherein said solution is a benzene solution.

25. A catalyst composition as defined in claim 23 wherein said solution is a cyclohexane solution.

26. A catalyst composition as defined in claim 1 wherein the nickel content is from about 0.001 to about five weight percent.

27. A catalyst composition as defined in claim 1 wherein the nickel content is from about 0.05 to about two weight percent.

28. A catalyst composition as defined in claim 14 wherein the nickel content is from about 0.001 to about five weight percent.

29. A catalyst composition as defined in claim 14 wherein the nickel content is from about 0.05 to about two weight percent.

30. A catalyst composition as defined in claim 1 wherein said contact of said support with said tris(cyclopentadienyl)trinickel dicarbonyl is effected at a temperature from about 20° to about 200° C. for about 10 minutes to about 12 hours.

31. A catalyst composition as defined in claim 1 wherein said contact of said support with said tris(cyclopentadienyl)trinickel dicarbonyl is effected at a temperature from about 20° to about 100° C. for about 15 minutes to about one hour.

32. A catalyst composition as defined in claim 14 wherein said contact of said support with said tris(cyclopentadienyl)trinickel dicarbonyl is effected at a temperature from about 20° to about 200° C. for about 10 minutes to about 12 hours.

33. A catalyst composition as defined in claim 14 wherein said contact of said support with said tris(cyclopentadienyl)trinickel dicarbonyl is effected at a temperature from about 20° to about 100° C. for about 15 minutes to about one hour.

34. A catalyst composition as defined in claim 1 wherein the solid tris(cyclopentadienyl)trinickel dicarbonyl is contacted with said support and a hydrocarbon solvent is then added.

35. A catalyst composition as defined in claim 34 wherein said hydrocarbon solvent is benzene.

36. A catalyst composition as defined in claim 34 wherein said hydrocarbon solvent is cyclohexane.

37. A catalyst composition as defined in claim 1 which is thereafter activated or preactivated by heating at a temperature of about 70° to about 200° C. for about five minutes to about four hours.

38. A catalyst composition as defined in claim 1 which is thereafter activated or preactivated by heating at a temperature of about 100° to about 170° C. for about twenty minutes to about one hour.

39. A catalyst composition as defined in claim 14 which is thereafter activated or preactivated by heating at a temperature of about 70° to about 200° C. for about five minutes to about four hours.

40. A catalyst composition as defined in claim 14 which is thereafter activated or preactivated by heating at a temperature of about 100° to about 170° C. for about twenty minutes to about one hour.

41. A catalyst composition as defined in claim 1 wherein said solution of a soluble salt is an aqueous solution.

42. A catalyst composition as defined in claim 1 wherein said solution of a soluble salt is an alcoholic solution.

43. A catalyst composition as defined in claim 1 wherein the cationic portion of said soluble salt is an alkali metal.

44. A catalyst composition as defined in claim 1 wherein the cationic portion of said soluble salt is an alkaline earth metal.

45. A catalyst composition as defined in claim 1 wherein the cationic portion of said soluble salt is a lanthanide.

46. A catalyst composition as defined in claim 1 wherein the anionic portion of said soluble salt is a halide.

47. A catalyst composition as defined in claim 1 wherein the anionic portion of said soluble salt is a nitrate.

48. A catalyst composition as defined in claim 1 wherein the anionic portion of said soluble salt is an acetate.

49. A catalyst composition as defined in claim 1 wherein the anionic portion of said soluble salt is an acetylacetonate.

50. A catalyst composition as defined in claim 43 wherein said alkali metal is potassium.

51. A catalyst composition as defined in claim 44 wherein said alkaline earth metal is magnesium.

52. A catalyst composition as defined in claim 45 wherein said lanthanide is lanthanum.

53. A catalyst composition as defined in claim 46 wherein said halide is chloride.

54. A catalyst composition as defined in claim 1 wherein said soluble salt is potassium acetate.

55. A catalyst composition as defined in claim 1 wherein said soluble salt is magnesium nitrate.

56. A catalyst composition as defined in claim 1 wherein said soluble salt is lanthanum chloride.

57. A catalyst composition as defined in claim 1 wherein said soluble salt is present in said solution in a concentration of from about 0.01 to about 1.0 molar.

58. A catalyst composition as defined in claim 1 wherein the amount of metal on said support after said support is contacted with said solution of a water soluble salt is within the range of about 0.1 to about 5.0 weight percent based on the final support.

* * * * *